United States Patent [19]

Lysaght et al.

[11] Patent Number: 4,964,976

[45] Date of Patent: Oct. 23, 1990

[54] OPTIMIZED FILTER AND METHOD

[76] Inventors: Michael J. Lysaght, 25400 Barsumian, Tower Lakes, Barrington, Ill. 60010; Daniel R. Boggs, 308 Amherst Ct.; Philip L. Ritger, 8 Parkside #4, both of Vernon Hills, Ill. 60061

[21] Appl. No.: 473,142

[22] Filed: Feb. 1, 1990

Related U.S. Application Data

[63] Continuation of Ser. No. 333,851, Apr. 4, 1989, abandoned, which is a continuation of Ser. No. 919,347, Oct. 15, 1986, abandoned.

[51] Int. Cl.$^5$ ............... B01D 61/14; B01D 61/24; B01D 63/02
[52] U.S. Cl. ............... 210/650; 210/739; 210/321.8; 210/321.89
[58] Field of Search ............... 210/321.87, 321.88, 210/321.89, 321.78, 321.79, 321.8, 646, 650, 651, 739; 604/4, 5, 6

[56] References Cited

U.S. PATENT DOCUMENTS

| Re. 32,089 | 3/1986 | Blatt et al. ............... 210/651 |
|---|---|---|
| 3,442,002 | 5/1969 | Geary, Jr. et al. ............... 210/321.89 |
| 3,612,282 | 8/1969 | Sing-Wang Cheng ............... 210/490 |
| 3,655,123 | 4/1972 | Judson et al. ............... 422/44 |
| 4,080,296 | 3/1978 | Clark ............... 210/323.1 |
| 4,082,658 | 4/1978 | Fritzsche et al. ............... 210/500.23 |
| 4,082,670 | 4/1978 | Joh ............... 210/456 |
| 4,105,731 | 8/1978 | Yamazaki ............... 210/321.89 |
| 4,124,509 | 11/1978 | Iijima et al. ............... 210/321.79 |
| 4,124,510 | 11/1978 | Joh ............... 210/321.8 |
| 4,187,180 | 2/1980 | Joh ............... 210/321.8 |
| 4,191,182 | 3/1980 | Popovich et al. ............... 210/321.65 |
| 4,201,673 | 5/1980 | Kanno et al. ............... 210/321.81 |
| 4,202,776 | 5/1980 | Joh ............... 210/321.8 |
| 4,212,742 | 7/1980 | Solomon et al. ............... 210/247 |
| 4,212,744 | 7/1980 | Oota ............... 210/321.64 |
| 4,214,990 | 7/1980 | Joh ............... 210/321.8 |
| 4,219,426 | 8/1980 | Spekle et al. ............... 210/321.8 |
| 4,231,877 | 11/1980 | Yamauchi et al. ............... 210/321.8 |
| 4,239,624 | 12/1980 | van Zon ............... 210/236 |
| 4,239,729 | 12/1980 | Hasegawa et al. ............... 422/48 |
| 4,240,907 | 12/1980 | Bentley ............... 210/646 |
| 4,268,279 | 5/1981 | Shindo et al. ............... 210/321.8 |
| 4,288,494 | 9/1981 | Porter et al. ............... 210/321.8 |
| 4,289,623 | 9/1981 | Lee ............... 210/321.78 |
| 4,293,418 | 10/1981 | Fujii et al. ............... 210/321.81 |
| 4,306,972 | 12/1981 | Denti et al. ............... 210/321.81 |
| 4,315,819 | 2/1982 | King et al. ............... 210/321.8 |
| 4,367,139 | 1/1983 | Graham ............... 210/321.9 |
| 4,374,802 | 2/1983 | Fukasawa ............... 210/321.8 |
| 4,381,775 | 5/1983 | Nose' et al. ............... 604/245 |
| 4,396,510 | 8/1983 | Hsei ............... 210/321.8 |
| 4,447,191 | 5/1984 | Bilstad et al. ............... 604/6 |
| 4,458,539 | 7/1984 | Bilstad et al. ............... 604/6 |
| 4,479,760 | 10/1984 | Bilstad et al. ............... 417/395 |
| 4,479,761 | 10/1984 | Bilstad et al. ............... 417/395 |
| 4,479,762 | 10/1984 | Bilstad et al. ............... 417/283 |
| 4,481,827 | 11/1984 | Bilstad et al. ............... 604/6 |
| 4,493,693 | 1/1985 | Bilstad et al. ............... 604/6 |
| 4,498,983 | 2/1985 | Bilstad et al. ............... 210/393 |
| 4,526,515 | 7/1985 | DeVries ............... 604/6 |
| 4,573,962 | 3/1986 | Troutner ............... 604/6 |
| 4,588,407 | 3/1986 | Isono et al. ............... 210/321.8 |
| 4,605,503 | 8/1986 | Bilstad et al. ............... 210/651 |
| 4,614,513 | 9/1986 | Bensinger ............... 210/651 |
| 4,639,353 | 1/1987 | Takemura et al. ............... 210/321.81 |

FOREIGN PATENT DOCUMENTS 0114698 8/1984 European Pat. Off. .
0175618 3/1986 European Pat. Off. .

*Primary Examiner*—W. Gary Jones

[57] ABSTRACT

A method and apparatus for optimizing parameters of a hollow membrane filter results in a relatively small filter when a predetermined, substantially constant, driving pressure drop is applied between the inlet and the outlet of the filter. The method includes simultaneous solution of a set of equations to specify fiber length, number and internal diameter. A system including a computer can make optimized filters in response to the determined parameters.

2 Claims, 8 Drawing Sheets

OPTIMIZED FILTER AND METHOD

This application is a continuation of application Ser. No. 333,851 filed Apr. 4, 1989 abandoned, which is a continuation of application Ser. No. 919,347, filed Oct. 6, 1986, abandoned.

TECHNICAL FIELD

The invention pertains to the field of filter design. More particularly, the invention pertains to the optimization of filters usable in the collection of blood components, especially plasma.

BACKGROUND OF THE INVENTION

The collection of only plasma from volunteer donors, as opposed to the collection of whole blood, is not widespread. As a result, much of the plasma now collected for fractionation purposes comes from paid donors, not volunteer donors. This circumstance can be attributed to several, interrelated factors. First, conventional disposable whole blood collection systems are not suited for the collection of relatively large pools of plasma from which the various therapeutic plasma proteins, such as albumin and AHF (anti-hemophilic factor), are obtained. On the other hand, conventional disposable plasma collection systems involve a process (called plasmapheresis) which is time-consuming and, in part for this reason, does not appeal to volunteer donors. Furthermore, during the plasmapheresis process, while the whole blood is being separated into red blood cells and plasma, the blood collection system (typically a series of integrally attached bags) is physically separated from the donor. Such physical separation requires procedures to minimize the risk of error when several donors are being processed simultaneously that one donor's red blood cells are not inadvertently returned to another donor. In addition, physical separation of the blood from the donor could potentially raise concerns in the collection staff of exposure to infectious agents in the collected blood if fluid drips or leaks occur.

Second, while on-line extracorporeal separation systems, in which the blood collection system is not physically separated from the donor during the collection procedure, are also known, such systems are generally expensive, complex, not "donor-friendly", and are generally unsuited for portable operation.

For example, a representative centrifuge-based system is disclosed in Judson et al. U.S. Pat. No. 3,655,123 entitled "Continuous Flow Blood Separator."

A representative membrane-based system is disclosed in Popovich et al., U.S. Pat. No. 4,191,182.

One system of membrane collection suitable for portable operation has been described in a published European Patent Application, Publication No. 0114698 published Aug. 1, 1984; entitled "Process and Apparatus for Obtaining Blood Plasma." In this system, a unit of blood is withdrawn from a donor into a set containing a membrane filter, tubing and a sterile blood container (such as a conventional blood bag). The whole blood is first passed through the filter. The plasma flows through the membrane filter and is collected in a separate plasma container. The remainder of the blood unit, which had passed from the inlet to the outlet of the filter, is accumulated in the sterile container. It can then be immediately returned to the donor.

In this approach, the pressure available for driving the filtration process and for propelling the blood from the inlet to the outlet of the filter is relatively small. This pressure includes the donor's venous pressure (which, with an inflated pressure cuff on the donor's arm, is on the order of 40 mm Hg) and available hydrostatic head (approximately 50 mm Hg) for a total pressure on the order of 90 mm Hg. These pressures may vary significantly from donor to donor. This can result in a relatively slow and variable plasma collection time. It also requires relatively large filters to function at the available low driving pressures. It can also be difficult to achieve precise anticoagulant flow proportional to blood flow with inexpensive and simple-to-use hardware.

Another membrane-based system is disclosed in a group of three U.S. Pat. Nos. 4,479,760 entitled "Actuator Apparatus for a Prepackaged Fluid Processing Module Having Pump and Valve Elements Operable in Response to Applied Pressures"; 4,479,761 entitled "Actuator Apparatus for a Prepackaged Fluid Processing Module Having Pump and Valve Elements Operable in Response to Externally Applied Pressures"; and 4,479,762 entitled "Prepackaged Fluid Processing Module Having Pump and Valve Elements Operable in Response to Applied Pressures," all issued to Bilstad et al. The system of the Bilstad et al. patents utilizes a disposable module containing a hollow membrane filter, a plasma container and other elements. A fixture is provided to receive the module during the donation cycle. Constant volume pumps in the fixture are provided to draw whole blood from the donor into the inlet side of the filter and to return the concentrated red cells to the donor from the outlet side of the filter. A single needle is used from both drawing the whole blood from the donor and returning concentrated red blood cells to the donor.

Various other types of membrane filters for plasmapheresis are also known. For example, U.S. Pat. No. 4,212,742 to Solomon et al. discloses a filtration device that utilizes planar membrane elements suitable for use with transmembrane pressures in a range of 180 mm Hg down to 100 mm Hg. U.S. Pat. No. 4,381,775 to Nose' et al. discloses a cylindrical filtration device that utilizes hollow membrane filters. The filter disclosed by Nose' et al. was intended to operate with transmembrane pressures in a range of about 50 mm Hg down to 8.5 mm Hg.

A commercially available, cylindrical membrane plasma filter in a set sold by Baxter Travenol Laboratories, Inc., the CPS-10. This filter is, relatively speaking, rather large. This filter has a fiber length in the order of 20 cm resulting in an overall length of about 29 cm. With an input blood flow rate of 70 ml/minute and a plasma output flow rate of 20 to 25 ml/minute, the internal diameter of each of the fiber members is about 320 microns, with 800 fibers needed. The CPS-10 filter is normally operated with an inlet port to outlet port pressure drop on the order of 70 mm Hg.

It would be desirable to make the collection of plasma a volunteer-based activity to a much greater extent than it is currently. The ability to provide filters having optimal performance characteristics, given the constraints of a "donor-friendly" blood collection system, would be a step forward toward this worthwhile objective.

SUMMARY OF THE INVENTION

In accordance with the invention, a method is provided of making a hollow membrane filter having selected optimal characteristics. An optimized filter is also provided. The filter has a fluid inlet, a fluid outlet and a filtrate output. A plurality of axially oriented hollow membranes extends between the fluid inlet and outlet.

In accordance with the method, system performance requirements are first specified. These include:

(1) Total collected plasma volume, $V_p$ (500–600 ml); and (2) Total collection, or processing time, $T_p$ (45–60 Minutes).

From these requirements, a projected average plasma collection rate, $Q_f$, can be calculated:

$$Q_f = 2V_p/T_p.$$

A plurality of system constraints can also be specified. These include:

(1) Draw volume, $V_B$ (500 ml);

(2) Maximum extracorporeal volume including whole blood and collected plasma, $V_e$ (900 ml);

(3) Blood draw rate from the donor, $Q_i$ (60–100 ml/minute);

(4) Number of draw/return cycles needed, $N_c$ (2 or 3 preferably);

(5) Inlet blood Hematocit, $H_i$ (average value of 45% selected); and (6) Outlet blood Hematocit, $H_o$ (typically 70%).

From these constraints the maximum plasma collection rate and the total processing time can be determined and compared with those specified as requirements. If they are significantly different, then modifications to the requirements or constraints will be needed before proceeding.

The operating pressure drop can be specified from the available working pressure less any viscous or hydrostatic losses in tubing and other fluid circuit elements.

Having specified the pressure drop and the plasma flow rate, the number of fibers (N), the useable filtering length (L) of each fiber and the internal diameter (D) of each fiber can be calculated. Three independent equations for plasma flow rate, hydraulic resistance, and critical pressure for onset of hemolysis can be simultaneously solved values of N, L, and D.

More particularly, the present method can be used to optimize the design of a hollow membrane filter usable to extract plasma from whole blood. In this instance, whole blood input flow rate to the filter can be set in a range of 75–100 ml/minute, preferably in a range of 90–100 ml/minute. The filter efficiency, E, which can be determined from:

$$E = (Q_f/Q_i(1-H_i/100))$$

is preferably in a range of 50–70% with two to three cycles preferred. The preferred draw volume/cycle is on the order of 500 ml of whole blood. The preferred total collected volume of plasma is in a range of 500–600 ml/donor. Total extracorporeal volume is limited to 900 ml.

Total system driving pressure during the return phase will preferably be on the order of 250 mm Hg so as not to rupture the blood container. Pressure drops across conventional donor needles are in a range of 50–65 mm Hg. With the blood collection container positioned below the donor, a hydrostatic head loss of about 50 mm Hg is typically present. Hence, available pressure to be applied across the filter is preferably in a range of 100–160 mm Hg.

In accordance with the present invention, the number (N) of fibers, the length (L) and the internal diameter (D) of each fiber can be optimized for the desired system performance requirements with respect to a selected criterion. Possible optimization criteria include:

(1) Optimization with respect to a minimum device cost;

(2) Optimization with respect to a minimum fiber spun length;

(3) Optimization with respect to a minimum fiber area;

(4) Optimization with respect to a maximum hemolysis safety factor;

(5) Optimization with respect to a maximum operating pressure drop; or (6) Optimization with respect to a selected combination of the above.

A preferred optimization criterion is maximum hemolysis safety factor obtainable at a preferred device pressure drop without an increase in device cost. Given this particular optimization criterion, filter parameters can be determined for various efficiencies (E) and pressure drops across the filter (P):

| Device | E | P (mmHg) | N | L (cm) | D (micrometer) |
|---|---|---|---|---|---|
| 1a | .727 | 100 | 3099 | 7.00 | 192 |
| 1b | .727 | 150 | 2290 | 7.00 | 180 |
| 2a | .667 | 100 | 2429 | 7.00 | 202 |
| 2b | .667 | 150 | 1731 | 7.00 | 198 |
| 3a | .605 | 100 | 1889 | 7.00 | 213 |
| 3b | .605 | 150 | 1347 | 7.00 | 209 |

Preferably, fibers with a nominal internal diameter on the order of 200 micrometers will be used. In this instance values of N and L for the above examples would be recalculated as follows:

| Device | E | P (mmHg) | N | L (cm) |
|---|---|---|---|---|
| 1a | .727 | 100 | 2881 | 7.88 |
| 1b | .727 | 150 | 1995 | 8.28 |
| 2a | .667 | 100 | 2465 | 6.82 |
| 2b | .667 | 150 | 1705 | 7.17 |
| 3a | .605 | 100 | 2117 | 5.83 |
| 3b | .605 | 150 | 1462 | 6.13 |

As can be seen from the above information, as the pressure drop across the filter is increased, the required number of fibers for a given set of parameters is reduced.

Further, in accordance with the invention, a system for making the optimized filters is provided. This system includes a display terminal for operator control and for entering the above-noted requirements and constraints. A programmable control unit receives the various input values. A stored program is utilized to calculate optimized values of N, L and D. These values can then be provided to a housing forming system and a fiber forming system. The appropriate housing and fibers can then be assembled in an assembly system.

The overall length of a filter optimized in accordance with the present method and selected criteria is on the order of 11 cm. The overall diameter is on the order of 4 cm.

Other features and advantages of the present invention will become readily apparent from the following detailed description, the accompanying drawings, and the appended claims.

DETAILED DESCRIPTION OF THE PREFERRED EMBODIMENT

A filter which embodies the features of the invention is well suited for use in many diverse environments. In the illustrated embodiment, it is shown in association with a self-contained, portable system 10 usable for the collection of blood components from donors. However, it should be understood that the present disclosure is to be considered as an exemplification of the invention, and is not intended to limit the invention to the specific embodiments or uses illustrated.

Figure 1:
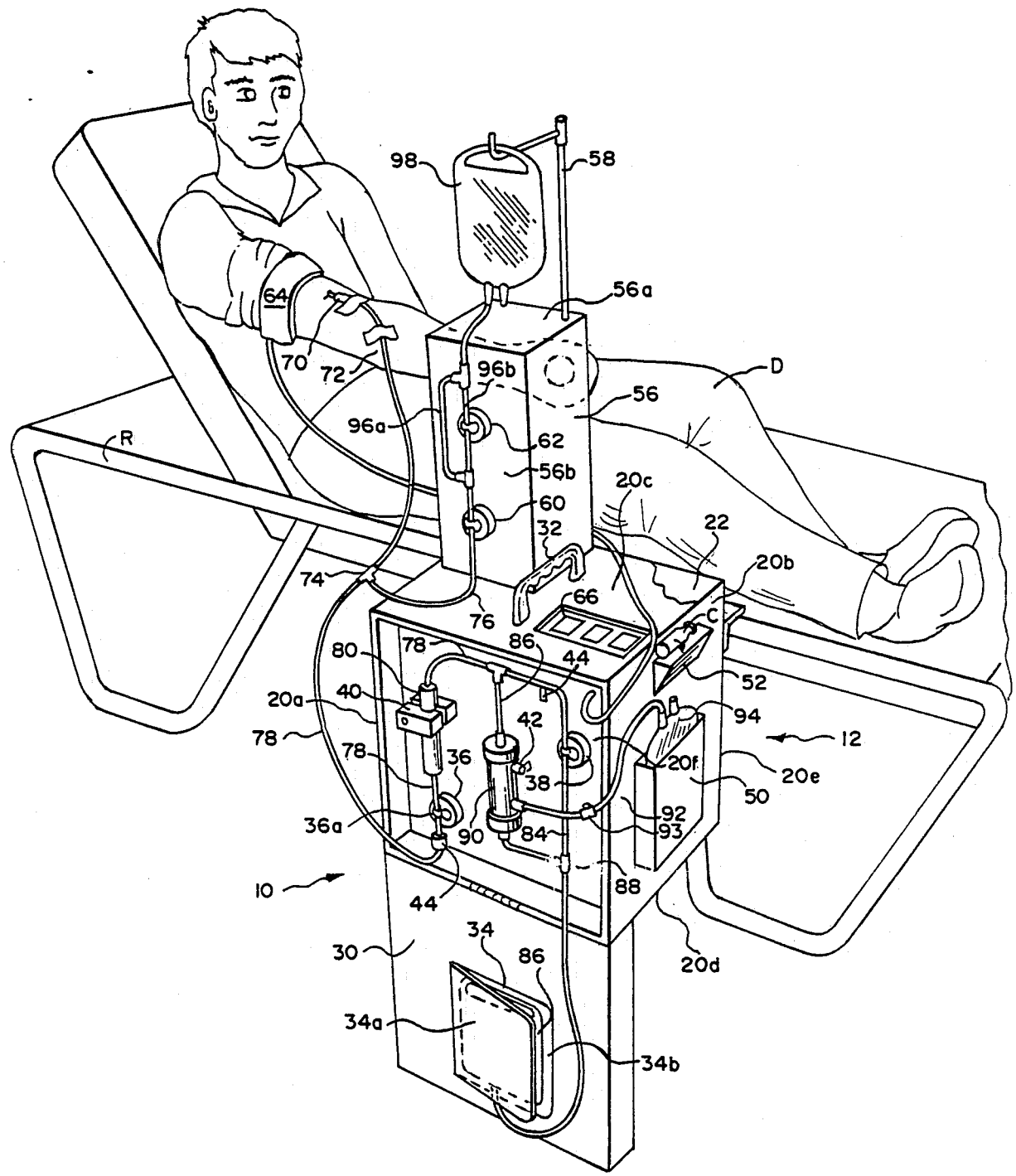
FIG. 1 is a perspective view of a plasmapheresis system, configured for use, in accordance with the present invention.
Figure 2:
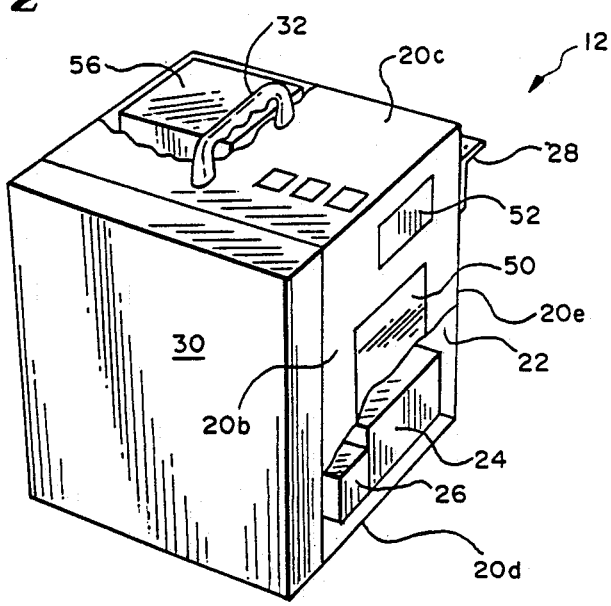
FIG. 2 is a perspective view, partly broken away of a fixture, configured for transportation, in accordance with the present invention.
Figure 3:
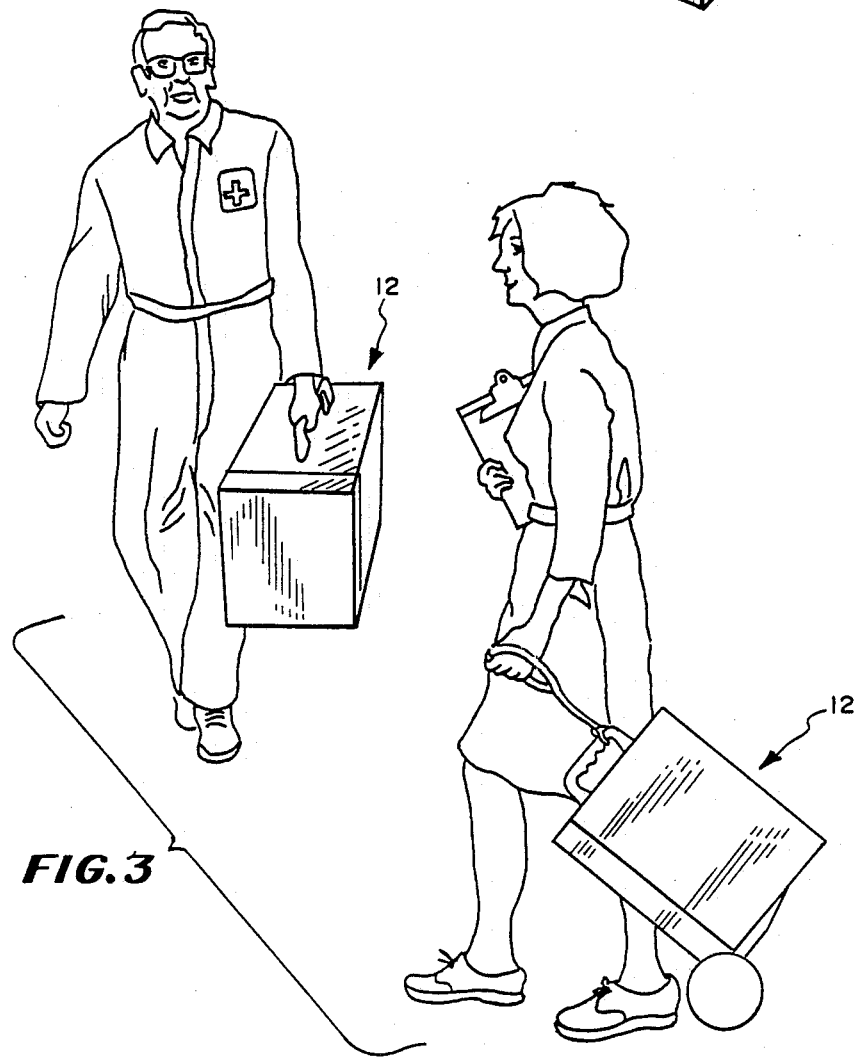
FIG. 3 is a pictorial view illustrating portability of the fixture in FIG. 2.

The self-contained, portable system 10 is illustrated in FIGS. 1 to 3. In the particular embodiment, the system 10 is intended to collect plasma from volunteer donors. In this embodiment, the system 10 includes a portable, self-contained and reusable fixture 12. The system 10 also includes a single-use, disposable, integrally-formed tubing set 14. The set 14 is mounted in the fixture 12 during the collection process.

The fixture 12 includes a housing 20 which can be formed of a metal or plastic. The housing 20 has sides 20a, 20b; a top and bottom 20c, 20d and rear surface 20e. Housing 20 defines or forms a closed interior region 22 in which is located a control unit 24 (see FIG. 2).

Affixed to the rear surface 20e is a pair of clamps 28. The clamps 28 are intended to engage a rail R of a blood donation cot or bed, as shown in FIG. 1. Such cots are currently regularly used in connection with the collection of whole blood from volunteer donors.

The clamps 28 support the fixture 12 at an appropriate working height without any need for supporting legs or tables. The clamps 28 fold flat against the rear surface 20e for storage and transportation.

The housing 20 has a hinged front cover 30. During transportation, the cover 30 is closed and latched. The overall size of the fixture 12 when closed for the transportation and storage is on the order of 12" wide by 12" deep by 14" high. A handle 32 is attached to the top surface 20c for use during transportation.

The hinged cover 30 holds, below the donor D, a whole blood collection container support or receptacle 34 with a hinged cover 34a. Located in the blood container support 34 is a force applying system 34b.

The fixture 12 also includes an energy source 51 for the force applying system 34b, as well as for the control system 24. The source 51 is self-contained in the housing 20, so that operation of the fixture 12 is independent of any external source of energy.

A recessed front panel 20f on the housing 20 supports clamps 36 and 38, a bubble sensor 40, a plasma separator support clamp 42 and tubing supports 44. The clamps 36, 38 are of a type conventionally used to close off flexible tubing members, and can take the form of pneumatically operated clamps. In this arrangement, in an unenergized condition, a spring biased clamping bar, such as the bar 36a, pinches the tubing in the clamp closed. When energized, by fluidic pressure, the clamping bar moves away from the tubing member permitting fluid to flow. The bubble sensor 40 is an ultrasonic sensor of a type conventionally used with blood donation and return systems to sense a gas-liquid interface. The sensor 40 is powered by a battery 26 housed within the interior region 22 (see FIG. 2).

Support 42 could be a spring clamp capable of removably supporting a cylindrical plasma separator such as a filter. Tubing supports 44 can correspond to small, L-shaped hangers of a type used to temporarily support flexible tubing.

Slidably affixed to the side 20b is a plasma container support 50. The support 50 can be a three-sided housing with a bottom but no top. Part of the side 20b forms the fourth side of the support 50. When the fixture 12 is being transported, the support 50 is pushed flat against the side 20b, as shown in FIG. 2.

While the energy source 51 can be variously constructed, in the embodiment shown in FIGS. 1 to 5, the source 51 includes a hinged cover and receiver 52. The receiver 52 can be opened to receive a module containing a releasable charge of energy. In the illustrated embodiment, the module takes the form of a $CO_2$ cartridge C inserted in the fixture 12 to provide a modular, self-contained fluidic, charge of energy to actuate the fluidic control system 24, the force applying system 34b, as well as the clamps 36, 38, 60 and 62. Alternately, the module can take the form of a battery, either single use or rechargeable.

A pop-up column 56 extends from the top 20c. The column 56 supports an L-shaped, tubular, anticoagulant support member 58 at a top surface 56a. The L-shaped support member 58 provides a hanger for a container of anticoagulant solution. The pop-up column 56, on a front surface 56b supports two additional tubing clamps 60 and 62. The clamps 60, 62, as is discussed subsequently, are used to regulate the flow of anticoagulant when the system 10 is in use. For storage or transportation, the tubular support member 58 is retractable into the column 56. The column 56 is in turn pushed downward into the region 22. The top surface 56a then is positioned adjacent the top 20c of the fixture 12.

An inflatable cuff 64 is provided, coupled to the control unit and timer 24. A control panel 66 with a plurality of push buttons is positioned on the surface 20c.

FIG. 2 illustrates the fixture 12 with the cover 30 closed and the column 56 retracted for storage and transportation. The fluidic control unit 24 and the battery 26 are also illustrated in FIG. 2 positioned in the interior region 22. The hangers 28 can be closed flat against the surface 20e during transportation.

FIG. 3 illustrates the portability of the fixture 12 when it is being taken to donation sites. The fixture 12 can be easily carried or pulled on a small cart of the type used to transport luggage. When the fixture 12 arrives at the donation site, it is mounted on the side of an available donor bed, as illustrated in FIG. 1 and opened. The tubing set 14 can be mounted in the fixture 12. The modular $CO_2$ cartridge C can be inserted in the receiver 52, and used to energize the fixture 12. No additional exterior source of energy is needed to actuate the fluidic control system 24, the force applying system 34b, and the clamps 36, 38, 60 and 62 of the fixture 12 to carry out the donation process. Provision can be made in the fixture 12 for a storage region in which additional cartridges can be kept prior to use.

As an alternate to the column 56, the housing 20 can be elongated and the clamps 60, 62 can be mounted on the recessed surface 20f, above the tubing member 78. In this embodiment, the clamps 60, 62 would be spaced apart horizontally from one another.

As an alternate to the clamps 28, the fixture 12 can be fitted with a pair of foldable or telescoping rear legs. In this embodiment, the foldable front cover 30, when opened, can function as a front support. The fixture 12 in this embodiment will be self-supporting and will stand on the floor beside the donor bed.

Figure 4:
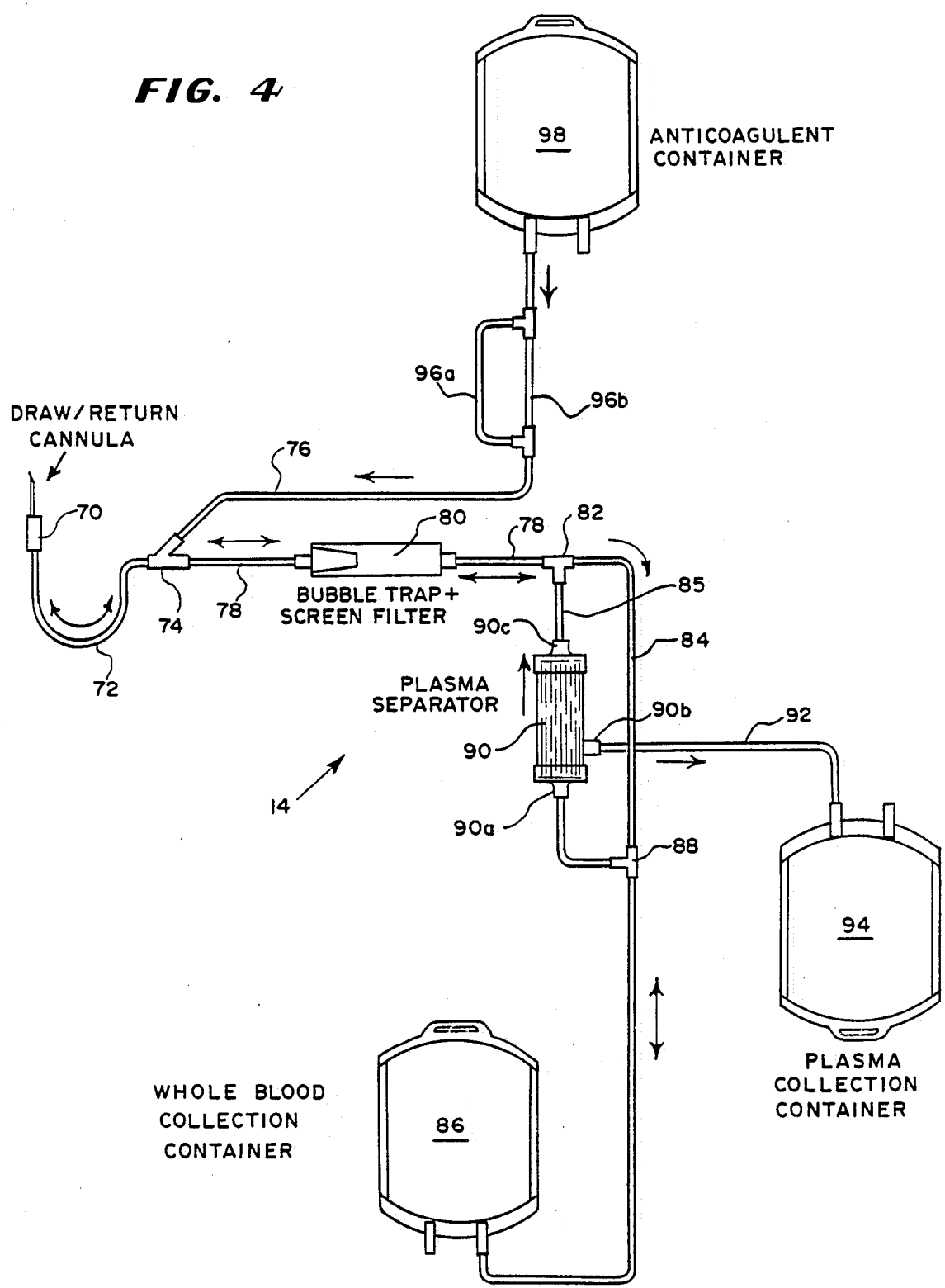
FIG. 4 is a planar view of a blood contacting set in accordance with the present invention.

FIG. 4 illustrates details of the set 14. The set 14 includes a single lumen draw/return cannula or phlebotomy needle 70. The cannula 70 has pointed end that can be inserted into a vein of a donor D, to provide access to the donor's whole blood.

The cannula 70 is coupled to a flexible fluid flow conduit or tubular member 72. The member 72 is coupled to a Y-shaped junction 74. The junction 74 is in turn coupled to an anticoagulant delivering tubular member 76 and a tubular member 78. The member 78 alternately receives whole blood from the cannula 70 and returns concentrated red blood cells to the donor D.

A combined bubble trap and screen filter unit 80 is located in the line 78. The unit 80 is conventional device manufactured by Travenol Laboratories, Inc.

A T-shaped coupling member 82 couples the tubing member 78 to tubing members 84 and 85. Tubing member 84 is in fluid flow communication with a whole blood collection container 86. The container 86 is preferably a variable volume container, meaning that the interior volume of the container expands to accommodate the introduction of fluid and can be contracted to reduce the interior volume so as to expel or displace the fluid contents. The variable volume container 86 can correspond to a flexible, conventional, blood collection bag. It can also correspond to a rigid or semirigid container which includes a collapsible portion to reduce its interior volume.

A T-shaped coupling member 88 is located in the line 84. The member 88 also places the collection bag 86 into fluid flow communication with an inlet 90a of a blood component separator 90, which, in the illustrated embodiment, separates plasma from the other components of whole blood, notably red blood cells, white blood cells, and platelets. The plasma separator 90 can be implemented in a variety of ways. For example, and without limitation, the separator 90 could be implemented as a chromotography column, an electrophoretic apparatus, an immunoabsorbant column or a membrane filter. The filter could incorporate planar membrane sheets, or cylindrical membrane fibers, and can also include a means for rotating the filter to enhance its filtration efficiencies. In a preferred form of the invention, the plasma separator is implemented as an optimized, hollow fiber membrane filter which embodies the features of the invention.

Coupled to and in fluid flow communication with a plasma output port 90b, via a flexible tubular member 92 is a plasma collection container 94. The container 94 could be a flexible plastic container similar to the container 86. An outlet 90c of the separator 90 is coupled to the tubular member 85.

The anticoagulant delivery member 76 is coupled via tubular members 96a and 96b to a container 98 of anticoagulant solution. The member 96a has a smaller internal diameter than does the member 96b. By means of these two flow paths, the anticoagulant can be easily and cheaply metered into the blood being collected via the tubing member 78. The arrows on FIG. 4 indicate directions of fluid flow when the set 14 is used with the fixture 12.

The tubing members of the set 14 can be formed of conventional, flexible plastic of a type suitable for contacting blood. The containers can be formed of conventional plastic now used in blood collection sets. Preferably, the set 14 comprises a sterile, integrally connected unit.

Figure 5:
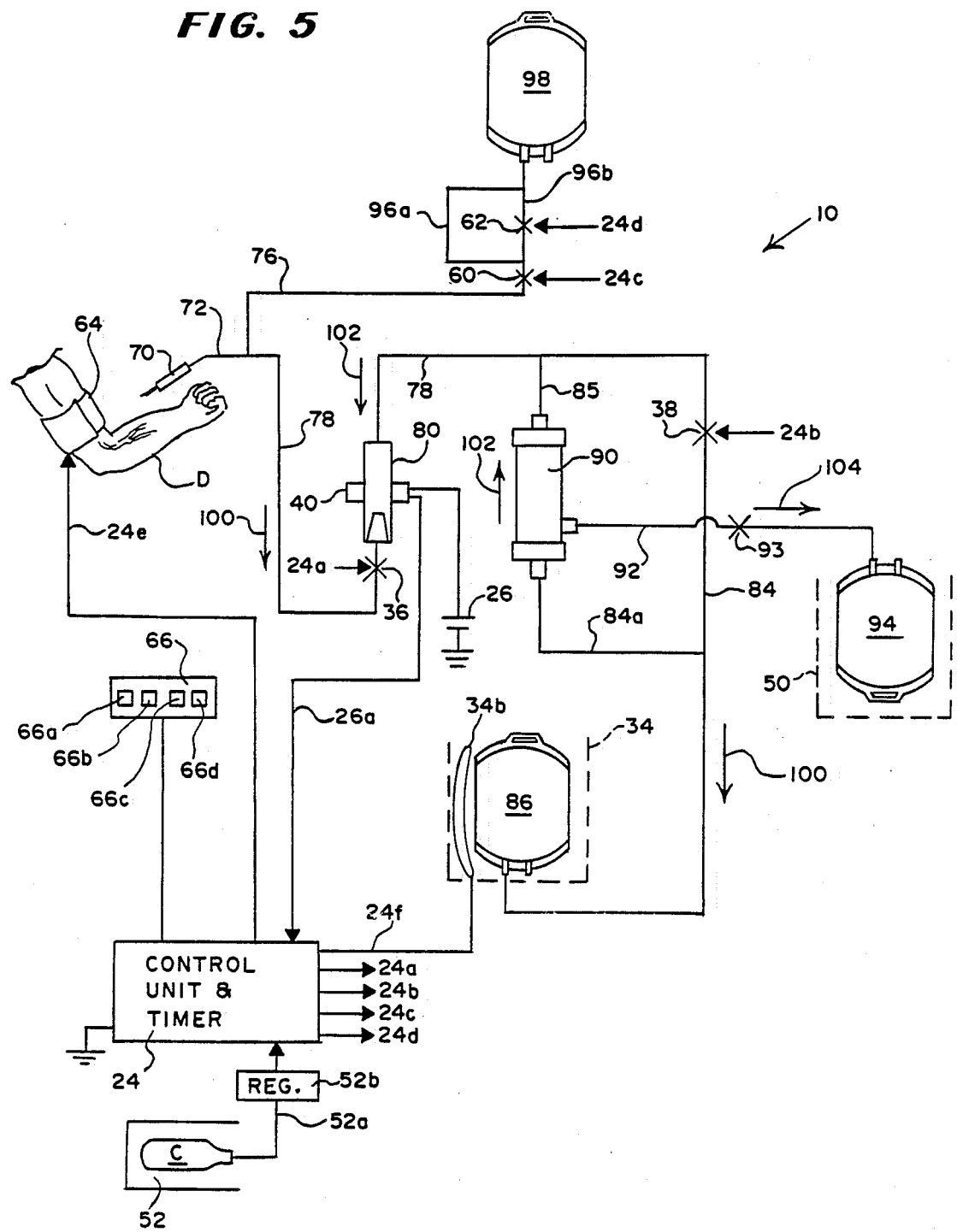
FIG. 5 is a schematic diagram of an apparatus and method for plasmapheresis in accordance with the present invention.

FIG. 5 illustrates the system 10 schematically. The fluidic control unit and timer 24 are coupled to the fluidic source of energy C via a fluid flow input line 52a and a regulator 52b. The control unit and timer 24 are also coupled via a plurality of fluid flow lines 24a, 24b, 24c and 24d the fluid actuatable clamps 36, 38, 60 and 62, respectively. The unit 24 can selectively open each of the clamps 36, 38, 60 and 62 by providing fluidic energy on the respective line 24a, 24b, 24c and 24d. Fluidic line 24e couples the unit 24 to the inflatable cuff 64.

The bladder 34b can be inflated and deflated by the unit 24 via a fluidic control line 24f. The control unit and timer 24 receive electrical signals on the line 26a from the battery powered bubble detector 40. If the electrical signal on the line 26a indicates that a bubble has been detected in the line 78 during a return cycle, as discussed subsequently, the control unit 24 will permit clamp 36 to close thereby blocking any further flow in the line 78 to the donor D. An alarm condition can also be indicated on the panel 66.

The control unit and timer 24 can be implemented of standard fluidic logic components in accordance with the donor and return cycle described herein. The electrical signal on the line 26a can be coupled to a solenoid valve in the unit 24.

FIG. 5 illustrates use of the mobile plasma collection system 10 in accordance with the present invention. The donor D is positioned adjacent to the sterile, sealed collection system 10. The system 10 includes the set 14 with the cannula 70, which could be a conventional, sterile single lumen phlebotomy needle of a type used in connection with blood collection. The needle 70 is coupled via flexible tubing 72, 78 and 84 of a conventional variety to the whole blood collection container or bag 86.

The collection bag 86 could be a flexible 500 ml plastic bag of a type now used for blood collection. The fluid operable clamp or valve 38 can be used to close off tubing member 84 under control of the unit 24. Closing the value 38 isolates the donor D from direct fluid flow communication from the container 86. Arrow 100 indicates the direction of flow of collected blood from the donor D into the collection bag 86. The whole blood drains from the donor D into the container or bag 86, as a result of the donor's internal blood pressure, which can be elevated in the region of the needle 70 by inflating the pressure cuff 64, as well as the force of gravity.

The container 86 is filled from the bottom as illustrated in FIGS. 1 and 5. Average fill time with a normal donor will be in a range of 4–7 minutes. The draw rate with an average donor will be in a range of 70–100 ml/minute.

Anticoagulant solution is metered from the container 98 through the two-part conduit 96a, 96b of known resistance. The anticoagulant solution is metered into the blood simultaneously with the whole blood being collected from the donor D.

The two tubes 96a and 96b each have a selected diameter and length. The tube 96a has a smaller diameter than does the tube 96b. By having both tubes 96a and 96b open simultaneously for a selected period of time and then closing one tube off while the other remains open, the rate of flow and quantity of anticoagulant mixed with the blood flowing through the member 72 can be regulated. Valve 62 can be used to close off the larger diameter conduit 96b under control of the unit 24. The dual tube system with members 96a, 96b makes it possible to keep the level of anticoagulant in the blood in the lumens of the tubing members, such as the member 78, and in the collection bag 86 between predetermined upper and lower limits even though donor blood rate is variable.

When the donor D has provided a unit of whole blood, the valves 60 and 38 are closed, and the inflatable cuff 64 is deflated. A force applying system 34b is then activated by the control unit 24. While the force applying unit can be variously constructed, in the illustrated embodiment, the force applying system takes the form of an inflatable bladder, is illustrated in FIG. 5. The force applying system 34b can alternately be of a type that is mechanically or electrically activated, in which case the energy source 51 could take the form of a battery.

The generator 34b applies a force to the variable volume collection bag 86 to reduce its volume. The whole blood accumulated in the collection bag 86 is thus expressed or forced, through a conduit 84a into the plasma separator 90. The separator 90 will separate out 40–70% of the plasma in the whole blood passed through.

The whole blood passes through the separator 90 due to the force generator 34b in the direction 102. The plasma accumulates at the output port 90b and travels via the flexible tubing or conduit 92 to the plasma collection container 94. An arrow 104 indicates the direction of flow of the plasma.

The concentrated red blood cells, or residual blood component, exit from the separator 90 via the conduit 85, enter the conduit 78 and pass through the bubble trap and screen filter 80. The control unit 24 continuously monitors the electrical signal line 26a. In the event a bubble is detected in the trap 80, the clamp 36 is deenergized. Clamp 36, due to its internal spring biasing, immediately closes and blocks further fluid flow in the line 78 toward the donor D. An alarm condition can be indicated on the panel 66 and the operator can take corrective action.

If no bubbles are detected, the concentrated red blood cells will be returned to the donor D via the line 78 and the same single-lumen cannula 70 used for whole blood collection. During the collection phase and the separation/return phase, the donor D is continuously coupled to the system 10 by means of the single-lumen cannula 70 and the bi-directional fluid-flow conduit 72, 78. The collection of plasma occurs simultaneously with the return of the red blood cells.

Due to the features of the invention, the whole blood passes through the separator 90 for separation, and the red blood cells are returned to the donor solely in response to the force applied to the bag 86 by the generator 34b, and without the application of any additional external force.

When the whole blood collection bag 86 has been emptied, a four to seven minute process, the plasma has been collected in the bag 94, and the remaining concentrated red blood cells have been returned to the donor D. The valves 38, 60, 62 can then be opened and the process repeated. The return rate of concentrated red blood cells is in a range of 40–80 ml/minute. Because the bag 86 is filled and drained from the bottom, all whole blood is expressed from the container. Depending on the rate of collection of plasma in the bag 94 the process may be repeated two or three times.

The relatively low cost of the interconnected set 14 is an advantage of the system 10. The interconnected plastic members can be used in the collection of plasma from a single donor and then thrown away. In addition, since the bag 86 containing the collected blood remains continuously connected to the donor D, there is no chance that a donor D will accidentally receive the blood of another donor. Further, because the system 10 is continuously coupled to the donor D, the possibility of contamination is minimized.

The container 86 can be prefilled with sterile saline. The saline can be flushed from the container and the system 10 prior to the initiation of the initial blood collection cycle. Flushing or priming with saline insures a gas free system.

Figure 6:
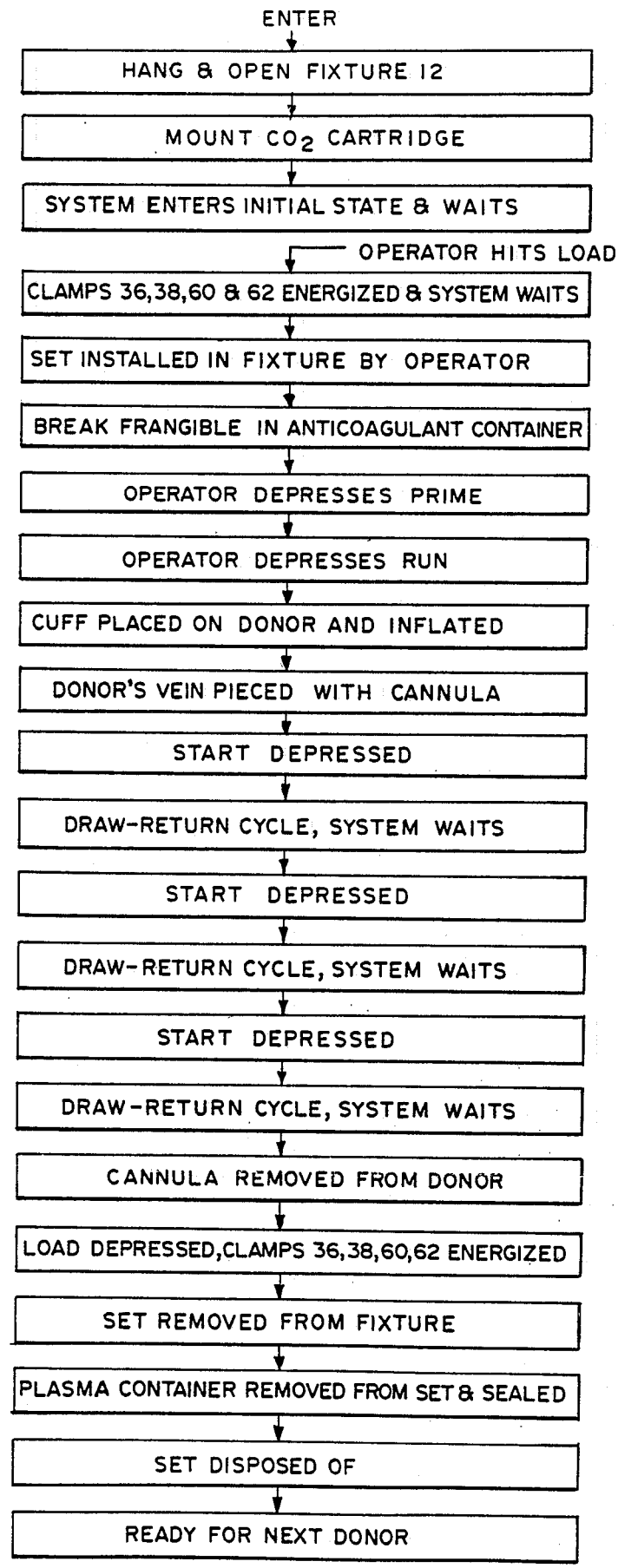
FIG. 6 is a flow diagram illustrating a method for plasmapheresis in accordance with the present invention.

An overall operational sequence is illustrated in the flow diagram of FIG. 6. The fixture 12 is hung on the donor bed the cover 30 opened. A $CO_2$ cartridge C is removed from storage in the fixture 12 and inserted into the receptacle 52. This energizes the control unit and timer 24 which enters an initial state. When the operator is ready, the LOAD button 66a can be depressed. Upon sensing depression of the LOAD button 66a, the unit 24 energizes all clamps 36, 38, 60 and 64. The operator then installs the set 14 in the fixture 12.

The operator can then open the anticoagulant container 98 permitting a fluid flow to fill the line 76. The operator then depresses the PRIME button 66b. Clamps 38, 60 and 62 automatically close. A manually operated clamp 93 is closed by the operator to prevent fluid flow through line 92. The unit 24 then energizes the bladder 34b, via the line 24f to force saline from the bag 86 through the line 84a, the separator 90 and the lines 85 and 78. After the separator 90 has been filled with saline, clamp 38 is energized to open the line 84 to the flow of saline. When the entire set 14 has been flushed (and bag 86 is empty), and saline has run out of the cannula 70, the operator depresses the RUN button 66c. The system 10 then deenergizes the bladder 34b and closes clamps 36 and 38.

The operator then places the cuff 64 on the arm of the donor D, and the cuff 64 is inflated by the control unit and timer 24. The operator then enters a vein in the arm of the donor D with the sterile cannula 70. This step places the set 14 in a bi-directional fluid flow communication with the donor. This communication is continuously maintained through the following draw and return cycles. The operator then depresses the START button 66d to initiate the first draw and return cycle.

The first draw-return cycle is then commenced and clamps 36, 38, 60 and 62 are automatically opened. The clamp 93 is also opened by the operator. Blood, mixed with anticoagulant, flows under the influence of gravity and the pressure cuff 64 into the container 86. The unit 24 can be set for a predetermined draw cycle; for example, seven minutes. When bag 86 contains the desired amount of whole blood (for example, 500 ml), the housing 34 will prevent additional inflow and no further blood will be drawn from the donor.

Part way through the seven minute draw cycle, clamp 62 is deenergized by the unit 24. The flow of anticoagulant is then decreased during the completion of the draw cycle.

At the end of the seven minute draw cycle, clamps 60 and 38 are deenergized by the unit 24 along with the cuff 64. The bladder 34b is energized by the unit 24. Whole blood is forced through the separator 90. Plasma is collected in the container 94 and simultaneously the concentrated red blood cells are returned to the donor D via the bi-directional fluid flow conduit 72, 78 and the single lumen cannula 70. When the system 10 has completed the return cycle, the clamp 36 is deenergized. The system 10 waits until the operator again presses the START button 66d. Once the START button 66d has been depressed, the unit 24 reinflates the cuff 64 and initiates the next draw cycle.

After the third draw-return cycle the container 94 will contain a desired volume, for example, 500 ml of plasma. Housing 50 limits the separated plasma to the desired volume. In the event the container 94 becomes filled with plasma prior to the end of the third draw cycle, the housing 50 will block further inflow of plasma. The remainder of the whole blood will then be returned to the donor D. The cannula 70 is removed from the arm of the donor D. The operator again depresses the LOAD button 66a. All of the clamps are then energized by the unit 24. The set 14 can then be removed. The plasma container 94 can be removed from the set 14 and sealed as is conventional. The remainder of the set can then be thrown away. The system 10 is then ready for the next donor.

As before stated, the force application system 34b can take the form of a variety of devices to produce the necessary expressing forces. For example, a standard spring actuated plasma expressor of a type marketed by the Fenwal Division of Travenol Laboratories, Inc., Model No. 4R4414, could be used to apply force to the collection bag 86 thereby forcing the whole blood through the separator 90. It has been found, however, that such a device exerts a force which expresses the whole blood from the container 86 with an output pressure that varies substantially with time as the container 86 is being emptied.

Preferably the separator 90 will be a hollow membrane fiber filter. It would be desirable from the point of view of optimizing the design of the filter 90 to be able to express the whole blood from the container 86 at a substantially constant, predetermined, pressure.

For purposes of the present disclosure, the phrase "substantially constant predetermined pressure" shall mean a selected, applied pressure that remains essentially constant during the time period during which the whole blood is being forced from the container 86. A pressure variation of 10 or 20% during the first 80 to 90% of the time during which the container 86 is being emptied would still come within the present definition of a substantially constant pressure system.

The system 10 is thus a constant pressure system as opposed to a constant volume system, in which a relatively constant volume of fluid is pumped through the system per unit of time. The system 10, as a constant pressure system, has the further advantage that if a line such as 84a, 85 or 78 becomes crimped or blocked during the return portion of a draw-return cycle, the pressure present therein will not increase as might be the case in a constant volume system.

Figure 7A:
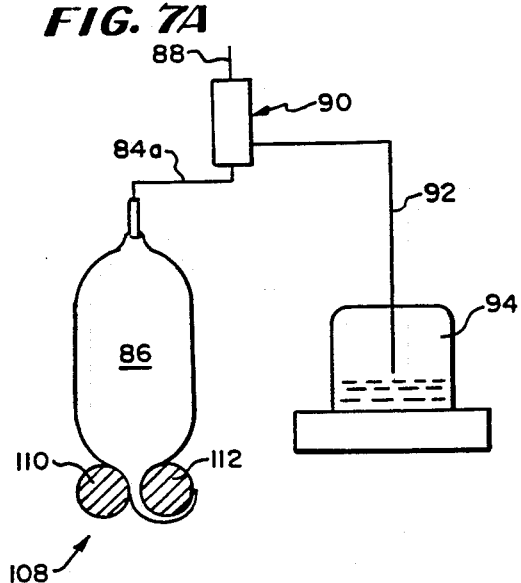
FIG. 7A is a side, schematic view of an apparatus for forcing whole blood out of the collection container.
Figure 7B:
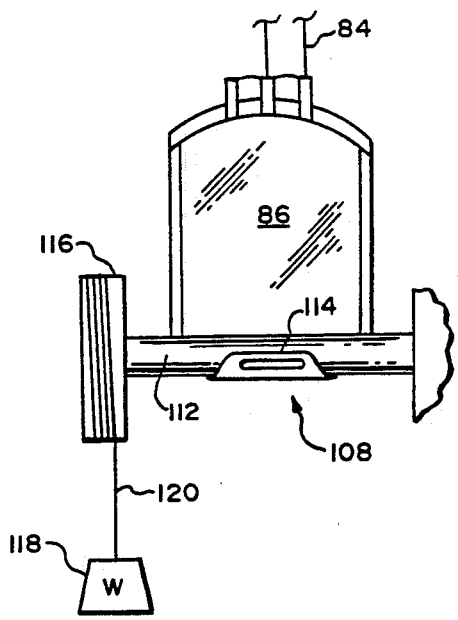
FIG. 7B is a front, schematic view of the apparatus of FIG. 7A.

A system 108 which will express the whole blood from the container 86 at a substantially constant predetermined pressure is illustrated in FIGS. 7A and 7B. This system 108, is formed with a pair of spaced apart rollers 110 and 112.

The rollers 110 and 112 are oriented so as to be parallel with a space there between. For example, the rollers might have a diameter on the order of ¾ of an inch and have an inter-roller gap of one-eighth of an inch. As illustrated in FIGS. 7A and 7B, a standard blood collection bag 86 is positioned with a lower tab located in a slot 114 in the roller 112.

In this embodiment, the self-contained energy source for the rollers 110, 112 includes means for releasably storing a quantity of energy to rotate the rollers 110, 112, as well as means for selectively introducing energy into the energy storage means.

While the above-described energy storage and introduction means can be variously constructed, as shown in FIG. 7B, they take the form of a pulley 116 attached to an end of the roller 112. A weight 118 is attached via a flexible cable or line 120 to the pulley 116. By recoiling the line 120 upon the pulley 116 after each use, the pulley 116 can be, in effect, "recharged" for subsequent use.

Experiments have indicated, that notwithstanding the fact that the blood container 86 is flexible and of irregular geometry, as the weight 118 unwinds due to the force of gravity, the force generating apparatus 108 will force the whole blood into the filter 90 at a substantially, constant pressure.

As the blood is forced from the bag 86, the empty portion of the bag 86 is wrapped around the roller 112. As the weight 118 continues to descend from the pulley 116, the bag 86 is continually drawn between the two rollers 110 and 112 and wrapped around the roller 112.

The system 108 will express the whole blood to the filter 90 at a substantially constant pressure on the order of 160 to 180 millimeters of mercury.

To generate pressures in a range of 160–180 mm of mercury, a weight 118 with a mass of 1950 g was used. The pulley 116 had a diameter of 15.9 cm. Larger or smaller pressures can be generated by varying the mass of the weight 118.

As the bag 86 empties, a spike of higher pressure appears after about 80% of the discharge or return period has passed. The effects of the spike can be attenuated by means of an elastic or stretchable, silicone tubing member attached to the weight 118 to slow its rate of descent during the last 20 percent of the discharge time. The presence of this spike does not preclude the roller system 108 from being a generator of substantially constant pressure as that phrase has been defined and used herein.

For example, a WACO 78170-10 elastic silicone tubing member was affixed to the weight 118. The time interval of substantially constant fluid pressure was, as a result, expanded from 80% to 90% of the discharge period. In this instance, a weight 118 with a mass of 4.81 kg was used in combination with a pulley 116 having a diameter of 5.71 cm.

Alternately, instead of using a weight such as the weight 118 as the energy source, a spring which exerts a constant force as it is being extended or as it is being retracted can be used to rotate the pulley 112. Such a spring, with a seven pound force has been used. It has been found experimentally that in connection with the system 108 the use of the constant force seven pound spring results in an output pressure on the order of 140 millimeters of mercury.

In this embodiment, the spring serves as the energy storage device which can be selectively recoiled, thereby "recharged", by the operator for subsequent use.

As an alternate to the roller system 108, and as earlier shown in the system 10 shown in FIG. 5, a commercially available inflatable bladder in a rigid container may be used. In this instance, the housing 34 of FIG. 1 corresponds to an external housing of the bladder 34b.

Figure 7C:
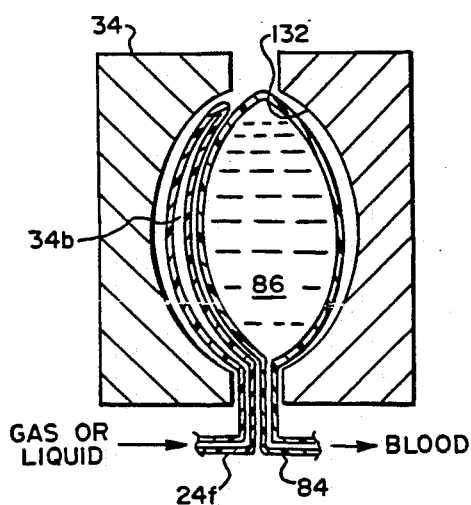
FIG. 7C is a side, schematic view of a preferred apparatus for forcing whole blood out of the collection container.

FIG. 7C illustrates a system utilizing such a force generating system. An external metal or rigid plastic housing 34 has a cavity 132 defined therein. The inflatable bladder 34b is positioned in the cavity 132. The blood collection bag 86 is placed in the cavity 132. Tubing 24f is provided to inflate the bladder 34b.

The bladder 34b is located adjacent the blood bag 86 and can be inflated by means of pressure from a gas or a liquid. For example, a regulated gas could be used, a liquid $CO_2$ cartridge could be used, or a gas or liquid under pressure due to a piston could also be used.

As the source of energy inflates the bladder 34b in the housing 34, the blood in the bag 86 is expressed into the tubing 84 at a substantially constant pressure. This pressure can be adjusted to be in a range of 160 to 180 millimeters of mercury as in the case with the dual roller system 108. The pressure should be adjusted in accordance with the resistance of the filter 90 and related flow circuits to provide physiologically acceptable return flow rates in a range of 40 to 80 cc per minute.

A further advantage of the bladder system is that the size of the cavity 132 and bladder 34b limit the volume of blood that can accumulate in the container 86. Hence, after the desired volume of blood has been accumulated in the container 86, the flow of whole blood essentially ceases. Similarly, housing 50 can be used to limit the volume of plasma that accumulates in the container 94.

In addition, unlike the system 108, the bladder system of FIG. 7C does not generate a spike of increased pressure and flow rate at the end of the return period. Instead, as the container 86 is emptied at the end of the return cycle, the generated pressure and flow rates decrease to zero.

Figure 8:
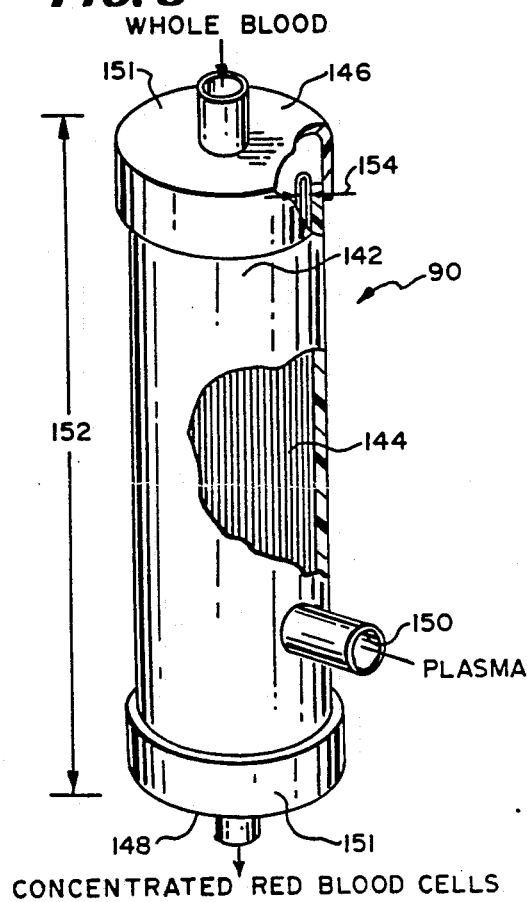
FIG. 8 is a fragmentary side view, partly in section, of a filter usable with the system of the present invention.

FIG. 8 illustrates an exemplary membrane filter usable with the system 10. The filter 90 includes a hollow cylindrical housing 142 which can be cylindrical with a circular cross section. The housing 142 could also have alternate shapes. It could, for example, have a square or rectangular cross section. In yet another alternate configuration, the filter 90 could be formed without a housing. The housing 142 could also be formed of a rigid plastic such as an acrylic or polycarbonate. In yet another embodiment, the housing could be formed of a flexible plastic such as plasticized poly(vinylchloride).

A plurality of hollow fiber membranes 144 is positioned, axially oriented in the housing 142. The housing 142 includes a blood inlet port 146, an outlet port 148 and a plasma output port 150. Fluid flow from the outlet port 148 is composed of concentrated red blood cells. This fluid can be regarded as a residual blood component. The plasma output port could also be located on either of the end caps 151.

The filter 90 has an overall length 152. This length is somewhat longer than the length L of each of the fibers to provide for filling the ends of the housing 142 with a potting compound.

The hollow fiber membranes, such as membranes 144, are suitable for contact with human blood and can be formed of polypropylene, poly(ethylene-co-vinyl alcohol), nylon, polysulfone or other materials. The fiber members 144 are oriented axially within the housing 142 such that the whole blood flows therethrough from end to end of the filter. The membranes are microporus and contain pores with diameters in a range of 0.1 to 5 microns preferably in a range of 0.2 to 0.6 microns. The membranes 144 need not be straight. If desired, for example, they could be mounted within a curved or circular housing to further conserve space.

Figure 9:
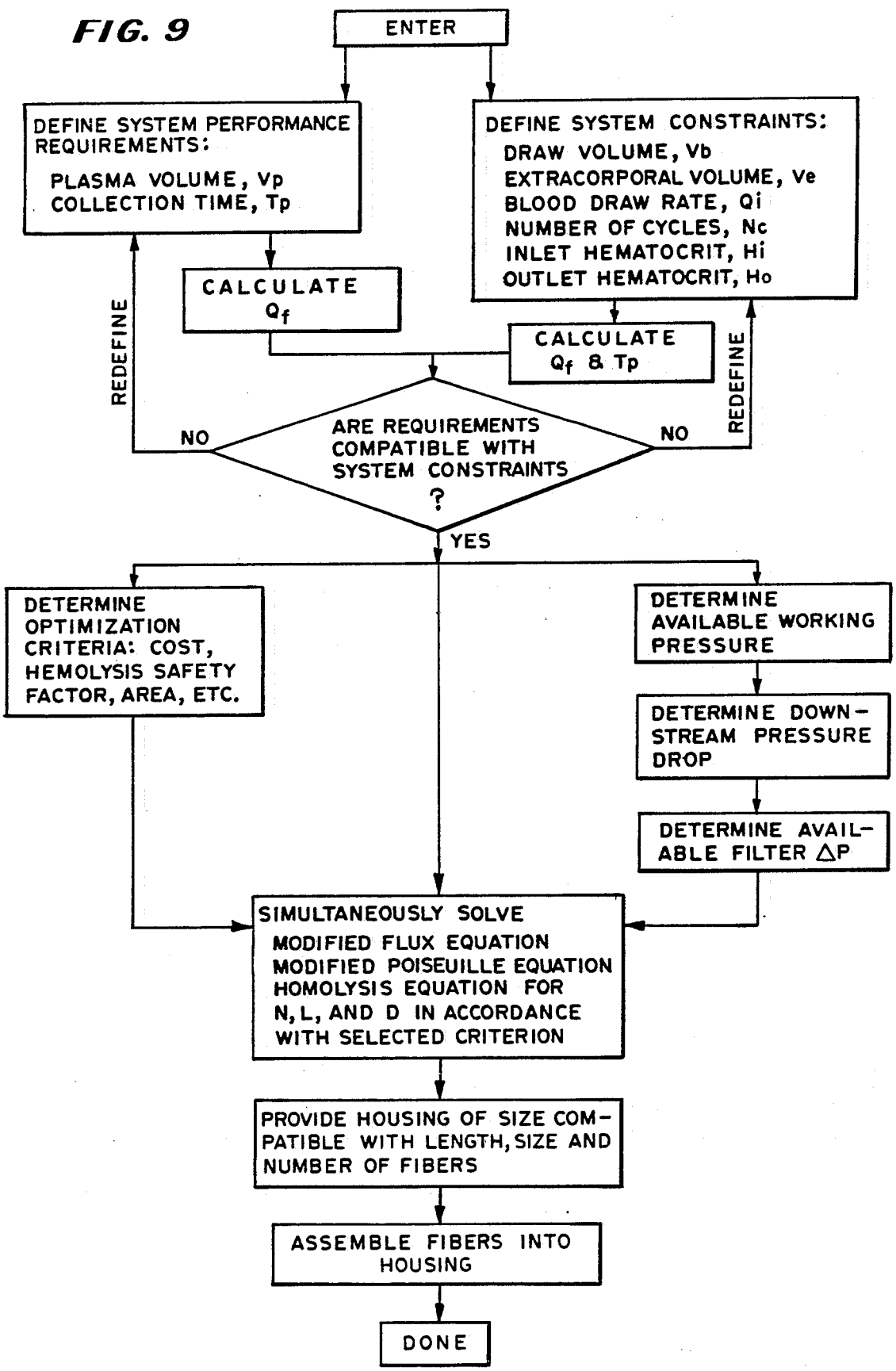
FIG. 9 is an over-all flow diagram of a method in accordance with the present invention.

In accordance with the present invention, the number (N) of membranes, the length (L) of each membrane and the internal diameter (D) of each such membrane can be optimized with respect to a selected criterion. FIG. 9 illustrates an over-all flow diagram of a method of making such an optimized filter.

In accordance with the method, system performance requirements must first be specified. These include the total plasma volume $V_p$ to be collected as well as the total collection time $T_p$.

A 500–600 ml total volume of plasma $V_p$ has become the desired volume to be collected/donor. Preferably, the total volume of plasma $V_p$ will be collected in a 30–45 minute time-frame $T_p$. This time-frame is believed to be donor-acceptable.

From these values, a range of plasma collection rates can be calculated using the equation:

$$Q_f = 2V_p/T_p$$

$Q_f$ is in a range of 22 to 40 ml/min. Using average values of $V_p$ and $T_p$, $Q_f$ is found to be 29 ml/min.

A plurality of system constraints can also be specified. These include:

(1) Draw volume, $V_b$. The volume of whole blood removed from the donor during each cycle. Prior experience with blood donation has resulted in a 500 ml unit of whole blood as the standard quantity per draw.

(2) Maximum extra corporeal volume, $V_e$: The maximum value of the sum of drawn whole blood not yet returned to the donor and the collected plasma. Prior experience indicates that a preferred value for $V_e$ is 900 ml.

(3) Blood flow rate from the donor, $Q_i$: The rate at which whole blood flows from the donor into the collection container. Prior experience indicates this rate to range from about 60 to 100 ml/min, with 90 ml/min being typical.

(4) Number of draw/return cycles, $N_c$: The number of times that the volume $V_b$ of blood is removed from the donor, processed, and returned. The value selected is related to $V_p$, $V_b$, and the efficiency of the plasma separation device.

(5) Inlet Blood Hematocrit ($H_i$). The volumetric concentration of red cells in the blood entering the filter. This value is set by donor physiology and rate of anticoagulant addition and is typically 0.45 (cc of red cells per cc of blood) or 45%.

(6) Outlet Blood Hematocrit ($H_o$): The volumetric concentration of red cells in the blood exiting the device and being returned to the donor. The value is determined by the filter efficiency. Since concentrated blood (high $H_o$) has a very high viscosity, excessive pressures may be required to return such blood to the donor. Thus a maximum allowable return hematocrit of about 0.75 or 75% is typically set.

From the above constraints, projected values of $Q_f$, $T_p$, and $V_p$ can be derived and compared with those specified previously as requirements.

For example,

Given a draw and return rate $Q_i$ on the order of 60-100 ml/min, preferably 90 ml, min, an inlet blood hematocrit of 0.45 and a maximum outlet hematocrit of 0.75, the plasma maximum flow rate can be calculated:

$$Q_f = Q_i(1 - H_i/H_o)$$

With the above values of $Q_i$, $H_i$, and $H_o$, the plasma flow rate is found to be 36 ml/min which is greater than that required.

The total processing time, $T_p$, can be calculated using the equation:

$$T_p = 2N_c V_b/Q_i$$

With $Q_i = 90$ ml/min and $V_b = 500$ ml, $T_p$ is 22.2 minutes for $N_c = 2$ and 33.3 minutes for $N_c = 3$.

The total amount of plasma collected, $V_p$, can then be calculated from the above values of $Q_f$ and $T_p$:

$$V_p = Q_f T_p/2$$

Using $T_p$ of 22.2 minutes ($N_c = 2$), a value of 400 ml is obtained; this is below the required 500-600 ml range.

Using $T_p = 33.3$ ($N_c = 3$), the amount of plasma collected is found to be 600 ml. This is an acceptable value relative to the requirements.

The maximum extracorporeal volume is given by:

$$V_e = V_b + (N_c - 1) V_p/N_c$$

With the above values of $V_b$, $N_c$, and $V_p$, $V_e$ is found to be 900 ml. This value of $V_e$ is the maximum allowable according to the above system constraints.

Since the requirements specify a range for collected plasma volume, the above considerations can be tabulated as in Table I where various filter/operating parameters are listed as a function of desired collection volume, $V_p$, for $N_c = 2$ and $N_c = 3$ with $Q_i = 70$ ml/min and $H_i = 0.45$.

TABLE I

| Number of Cycles ($N_c$) | $V_p$,ml | $Q_f$, ml/min. | F | E | $H_o$ | $V_e$,ml. | $T_p$,min. |
|---|---|---|---|---|---|---|---|
| 2 | 600 | — | .60 | 1.09 | — | — | — |
|   | 550 | — | .55 | 1.00 | — | — | — |
|   | 500 | 45.0 | .50 | 0.909 | 90.0 | 750 | 22.2 |
|   | 450 | 40.5 | .45 | 0.818 | 81.8 | 725 | 22.2 |
|   | 400 | 36.0 | .40 | 0.727 | 75.0 | 700 | 22.2 |
| 3 | 600 | 36.0 | .40 | 0.727 | 75.0 | 900 | 33.3 |
|   | 550 | 33.0 | .367 | 0.667 | 71.0 | 867 | 33.3 |
|   | 500 | 30.0 | .333 | 0.605 | 67.5 | 833 | 33.3 |
|   | 450 | 27.0 | .300 | 0.545 | 64.3 | 800 | 33.3 |
|   | 400 | 24.0 | .267 | 0.485 | 61.4 | 767 | 33.3 |

The $Q_f$ column corresponds to the expected plasma flow rate with input whole blood flow rate $Q_i = 90$ ml/min. F is the filtration fraction defined by $F = Q_f/Q_i$. E is the device efficiency, the ratio of the amount of plasma removed to the total amount available.

$$E = \frac{Q_f}{Q_i(1 - H_i)}$$

The $H_o$ column corresponds to the expected hematocrit of the concentrated red blood cells or residual component flowing from the filter outlet. The $V_e$ column specifies the total maximum extracorporeal volume as a result of the constraints and independently adjustable parameters. The $T_p$ column specifies the expected processing time for the specified number of cycles $N_c$.

Using Table I various possible filters can be evaluated with respect to the system performance requirements, the constraints and the ability to make such a filter. For example, the top two entries in Table I have efficiencies, E, equal to or greater than 1.0. They are of course unbuildable.

When it has been determined that for one or more possible filters, the performance requirements are compatible with the system constraints the various system pressures can then be considered.

Pressure needed to force the collected whole blood through the filter can be determined from summing the sources and sinks or drops of pressure in the return system:

$$P_A - P - P_N - P_H - P_X = 0$$

Where $P_A$ corresponds to the pressure generated by the force applying system 82, P corresponds to the pressure drop across the filter 90, $P_X$ corresponds to any other pressure losses in the return lines 84a, 85, 78, $P_N$ the donor needle 70 and $P_H$ corresponds to any pressure head that must be overcome due to the donor D being elevated with respect to the blood container 86.

$P_H$ is typically about 50 mmHg with the collection bag positioned below the donor. Losses in the return lines are essentially negligible. Losses due to the donor needle 70 at the expected flow rates are on the order of 50 mm Hg.

The burst strength of standard 500 ml blood collection containers, such as the container 86, is in excess of 250 mm Hg. Hence, $P_A$ can be set to 250 mm Hg without bursting the container 86. This results in 150 mm Hg pressure that can be applied across the filter 90. This is about three times the pressure drop available to drive the whole blood through the filter in the previously noted gravity driven, membrane pheresis system.

In a preferred mode the plasma collection container 94 is preferably located as illustrated in FIG. 1, at the same height with respect to the filter 90. This minimizes the filtrate chamber pressure contribution to the transmembrane pressure.

Transmembrane pressure in this preferred configuration ranges from 200 mm/Hg at the inlet port 146 to 50 mm/Hg at the outlet port 148. In contrast to the present filter, Nose' et al. operated with a transmembrane pressure in a range below 50 mm/Hg. Soloman et al. operated with an input flow rate of 270 ml/minute, an inlet transmembrane pressure of 180 mm/Hg and an outlet transmembrane pressure of 100 mm/Hg.

To determine the number (N) of fibers, the length (L) and the internal diameter (D) of the fibers, three simultaneous design equations must be solved. These three equations are:

(1) An Empirically Modified Form of an equation for filtrate fluorate first proposed by Zydney and Colton and published in "Continuous Flow Membrane Plasmapheresis: Theoretical Models for Flux and Hemolysis Prediction," *Trans. Am. Soc. Artif. Intern. Organs*, 28, 408 (1982):

$$Q_f = K_1 Q^x N^{(1-x)} L^{(1-y)} D^{(1-3x)}$$

where $$K_1 = 0.0002206 \, [\ln(95/h_i)]^z \pi^{(1-x)} (8/15)^x$$

x = 0.9141
y = 0.3619
z = 0.8528
Q = $Q_i - Q_f/2$ = average blood flow rate
$H_i$ = inlet hematocrit, %

(2) Hagen-Poiseuille equation, a hydraulic resistance related equation, with a psuedo viscosity/Hematocrit function $$Q = \frac{K_2 \, PND^4}{\mu(L + L_p)}$$

where
$\mu$ = viscosity function = $3.236206/[(1 - H_i)/100]^{1.440442}$
$L_p$ = potting length, cm
P = available pressure drop, mmHg $$K_2 = \frac{(\pi)}{(128)^*} \text{ (conversion factor for consistent units)}$$

(3) Hemolysis/Shear Rate Relationship $$HSF = \frac{(TMP)_h}{P - (-20 \text{ mmHg})}$$

where $$(TMP)_h = (3.51E - 9 \, \gamma_{w,h}^3 - 0.00003 \, \gamma_{w,h}^2 + 0.0976 \, \gamma_{w,h} + 4.75)/r_p$$

$r_p$ = average pore radius and (−20 mmHg) is a typical filtrate collection chamber pressure.

For a specified hemolysis safety factor, HSF, inlet blood hematocrit, $H_i$, pressure drop, P, inlet blood flow rate, $Q_i$, and filtration rate, $Q_f$ a unique combination of N, L, and D can be determined as follows:

The Hemolysis/Shear Rate relationship can be solved for a unique value of the wall shear rate for hemolysis, $\gamma_{w,h}$.

The wall shear rate for hemolysis can be related to the device average wall shear rate, $\gamma w, Q$ $$\gamma w, Q = \frac{Q}{Q_i} \gamma_{w,h} = \frac{8 Q}{15 \, ND^3 \pi}$$

from which it can be determined that:

$$N = \frac{8}{15} \, \frac{Q_i}{\gamma_{w,h} \pi D^3} \quad (1)$$

The Hagen-Poiseuille Equation provides the following expression for M $$N = \frac{Q\mu}{K_2 P} \, \frac{(L + L_p)}{D^4} \quad (2)$$

Equating equations (1) and (2) yields $$D = K_3 (L + L_p) \quad (3)$$

$$\text{where } K_3 = \frac{15}{8} \, \frac{Q}{Q_i} \, \frac{\gamma_{w,h} \pi \mu}{K_2 P}$$

From the modified Zydney-Colton filtrate flow rate equation the following expression for N can be determined:

$$N^{(1-x)} = \frac{Q_f}{K_1 Q^x} \, \frac{1}{L^{(1-y)} D^{(1-3x)}} \quad (4)$$

Substituting N from equation (2) into equation (4) yields:

$$D = \left[ K_4 * \frac{(L + L_p)^{(x-1)}}{L^{(1-y)}} \right]^{\frac{1}{(x-3)}} \quad (5)$$

$$\text{where } K_4 = \left[ \frac{K_2 P}{\mu} \right]^{(1-x)} \frac{Q_f}{K_1 Q}$$

Equating equations (3) and (5) yields the following function for L:

$$f(L) = K_3(L + L_p) - \left[ K_4 \frac{(L + L_p)^{(x-1)}}{L^{(1-y)}} \right]^{(1/x-3)} = 0 \quad (6)$$

which can be solved for L using a Newton-Raphson routine.

The value of L obtained from equation (6) is substituted into equation (3) to solve for D and finally, the values of L and D are substituted into equation (2) to solve for N.

In accordance with the present invention, the number (N) of fibers, the length (L) and the internal diameter (D) of each fiber can be optimized for the desired system performance requirements with respect to a selected criterion. Possible optimization criteria include:

1. Optimization with respect to a minimum device cost;
2. Optimization with respect to a minimum fiber spun length;
3. Optimization with respect to a minimum fiber area;
4. Optimization with respect to a maximum hemolysis safety factor;
5. Optimization with respect to a maximum operating pressure drop; or
6. Optimization with respect to a selected combination of the above.

A preferred optimization criterion is to maximize the hemolysis safety factor obtainable at a preferred device pressure drop without an increase in device cost.

In order to carry out this optimization, fiber spun length must be considered. The fiber spun length, $L_s$ can be determined in accordance with the following equation:

$$l_s = N(L + L_p + L_w) \quad (20)$$

where $L_w$ is the length of waste fiber required for manufacturing of filter device, is directly proportional to device cost. $L_p$ is referred to as the "potting length". This is the end length of each fiber that is covered by a urethane or epoxy material. The potting length is inoperative for filtration purposes but contributes to the spun length $L_s$.

For a fixed preferred device pressure drop, a minimum in spun length as a function of hemolysis safety factor occurs. From the hemolysis/shear rate relationship, it can be determined that the hemolysis safety factor is directly proportional to the wall shear rate for hemolysis. Thus, in accordance with the preferred optimization criterion, the spun length, $L_s$, is minimized with respect to wall shear rate for hemolysis, $\gamma_{w,h}'$ for a preferred device pressure drop. This involves solving the following equation for $\gamma_w$ and L:

$$\frac{dL_s}{d\gamma_{w,h}} = \frac{\partial L_s}{\partial N} \frac{dN}{d\gamma_{w,h}} + \frac{\partial L_s}{\partial L} \frac{dL}{d\gamma_{w,h}} = 0 \quad (7)$$

Equation (7) involves an interactive solution utilizing a simultaneous Newton-Raphson routine for $\gamma_w$ and L. Equation (7) provides the basis for a computer based program, noted below, usable in the determination of values of N, L and D for plasma separation filters such as the filter 90.

Use of the above parameters and equations results in the following filter parameters optimized in accordance with the above selected criteria for selected values of pressure applied across the filter.

TABLE II

| P (mmHg) | N | L (cm) | D (micrometers) |
|---|---|---|---|
| 100 | 3099 | 7.00 | 192 |
| 150 | 2209 | 7.00 | 189 |
| 100 | 2492 | 7.00 | 202 |
| 150 | 1731 | 7.00 | 198 |
| 100 | 1889 | 7.00 | 213 |
| 150 | 1347 | 7.00 | 209 |

Use of a filter with one set of the above parameters will result in extraction of 50 to 70% of the plasma in the whole blood which passes through the filter. Table II also illustrates in each instance the driving pressure drop P between the inlet 146 and the outlet 148 of each filter design. As can be seen, the number of fiber membranes decreases as the pressure drop across the filter is increased. Care must always be taken to insure that the force generating systems provide enough pressure at the outlet port 148 to return the filtered blood to the donor D.

The present method and apparatus are particularly advantageous in that, given a substantially constant input pressure, the design and characteristics of the hollow fiber filter 90 can be optimized pursuant to a selected criterion. In addition, the sterile system 10 can be configured to use a disposable set that is relatively inexpensive. The sterile system 10 is easy to use and is portable to church basements or recreation halls where blood collection centers are often temporarily established.

Figure 10:
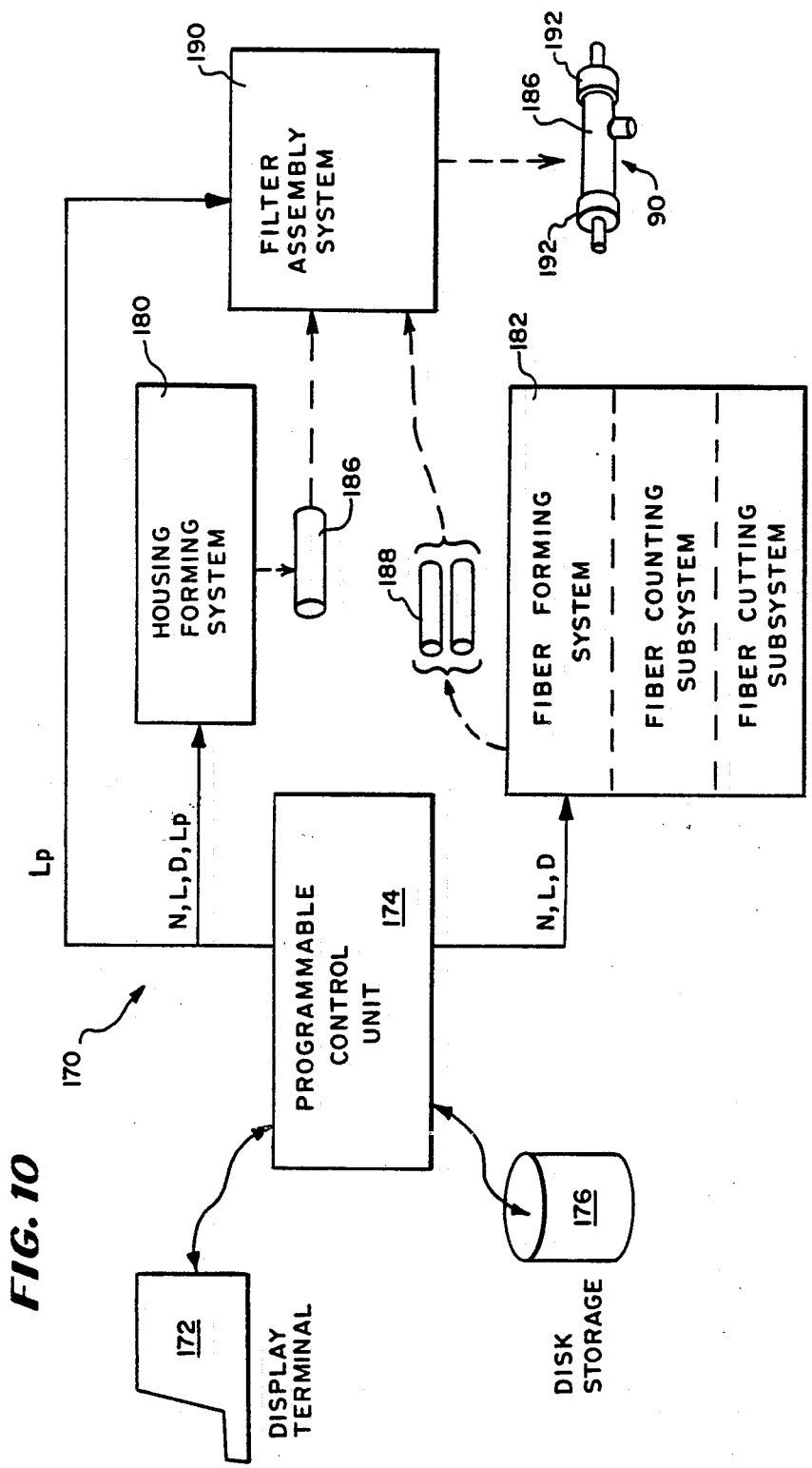
FIG. 10 is a block diagram of a system for making optimized filters in accordance with the present invention.

A system 170 for determining parameters of and assembling optimized filters is illustrated in block diagram form in FIG. 10. A manually operable display terminal 172 can be used to enter the above-noted performance characteristics and constraints through a keyboard. The display terminal is coupled to a programmable control unit 174, such as a Hewlett-Packard Model 9836. A disk storage unit 176, coupled to the control unit 174, can be used to store a control program for determining N, L and D in accordance with the above-noted method.

Attached hereto as Exhibit A and made a part of this specification is a control program written in BASIC with attached output results. This control program can be stored on the disk storage unit 176. The control program will determine optimized values of N, L and D in accordance with the above method and the selected criterion.

The optimized values of N, L and D generated by the control unit 174 using the attached program and the potting length Lp can be supplied to a housing forming system 180 and a fiber forming system 182. The housing forming system 180 can provide a housing 186 of a length and internal diameter to contain the selected number N of hollow fiber membranes each having a length L and internal diameter D. Housings can be formed injection or blow molding. Alternately, an extruded rod having a cross section that is circular or in the shape of a parallelogram can be cut to the desired length.

The fiber forming system 182 can provide a plurality 188 of hollow membrane fibers. The process of fabrication of hollow membrane fibers with a selected internal diameter D usable for separation of a fluid component is well known. The fiber forming system can also cut the fiber to the correct length L and collect the desired number N of such fibers.

A filter assembly system 190 can assemble the fibers 188 within the housing 180. In a preferred form of practicing the invention, the fibers are assembled axially in a cylindrical housing. The assembly system can also provide end caps such as caps 192 to seal the fibers 188 within the housing 186 thereby forming the assembled filter 90.

From the foregoing, it will be observed that numerous modifications and variations can be effected without departing from the true spirit and scope of the novel concept of the present invention. It is to be understood that no limitation with respect to the specific embodiments illustrated herein is intended or should be inferred. It is, of course, intended to cover by the appended claims all such modifications as fall within the scope of the claims.

EXHIBIT A

```
10    !!!!!!!!!!!!!!!!!!!!!!!!!!!!!!!!!!!!!!!!!!!!!!!!!!!!!!!!!!!!!!!!!!!!!
20    !                    N.L.D OPTIMIZATION PROGRAM                     !
30    !!!!!!!!!!!!!!!!!!!!!!!!!!!!!!!!!!!!!!!!!!!!!!!!!!!!!!!!!!!!!!!!!!!!!
40    OPTION BASE 1
50    DEG
60    PRINTER IS 701
70    DATA 33.0,90,45,2.5,0.3             !Qf,Qin,H,Lp,Rp
80    DATA .9141,.3619,.8528              !Coefficients for flux equation
90    READ Qf,Qin,H,Lp,Rp
100   READ X,Y,Z
110   !
120   Qbar=(Qin-Qf/2)
130   Qout=Qin-Qf
140   Hbar=H*(1+Qin/Qout)/2
150   Visc=FNVisc(Hbar)
160   !
170   IMAGE 10X,DDDDD,5X,DD.DD,5X,DDD,4X,DDDDD,4X,DDDDD,5X,D.DD,5X,D.DDD
180   PRINT USING "10/"
190   PRINT "                        3 CYCLE DEVICES"
200   PRINT
210   PRINT "             Plasma volume collected........ 550 ml"
220   PRINT "             Proceesing time................ 33.3 min"
230   PRINT
240   PRINT "             Blood volume drawn per cycle... 500 ml"
250   PRINT "             Maximum Extracorporel Volume... 866 ml"
260   PRINT "             Blood flow rate................ 30 ml/min"
270   PRINT
280   PRINT "             Filtration Fraction............ 0.367"
290   PRINT "             HCT............................ 45%"
300   PRINT "             Efficiency..................... 0.667"
310   PRINT "             Plasma Flow rate............... 33.0 ml/min"
320   PRINT "             Potting length................. 2.5 cm"
330   PRINT USING "6.5/"
340   !
350   !
360   K2=.0002206*(LOG(95/H)^Z)
370   K2=K2*PI*(8/(15*PI))^X
380   K3=60*100*PI/(16*.00075*8)
390   !
400   !
410   FOR I=1 TO 5
420     P=50+(I-1)*50
430   PRINT "           DEVICE INLET PRESSURE............";P;"mmHg"
440   PRINT
450   PRINT "          N        L        D       Ae       At       Rh       Ls"
460   PRINT
470   !
480   K4=K2*Qbar/Qf
490   K4=K4*(Visc/(K3*P))^(1-X)
500   !
510   Delta=.1
520   Gamma1=400+(I-1)*50
530   LOOP
540   K5=15*Gamma1*PI*Visc*Qbar/(8*K3*Qin*P)
550   Lg1=12
560   LOOP
570   Func1=(K5*(Lg1+Lp))-((Lg1+Lp)^(X-1)/(K4*(Lg1)^(1-Y)))^(1/(X-3))
580   EXIT IF ABS(Func1)<.00000001
590   Func2=(K5*(Lg1+Delta+Lp))-((Lg1+Delta+Lp)^(X-1)/(K4*(Lg1+Delta)^(1-Y)))^(1/(X-3))
600   Lg2=Lg1-Delta*Func1/(Func2-Func1)
610   Lg1=Lg2
620   END LOOP
630   D1=K5*(Lg1+Lp)
640   N1=8*Qin/(15*Gamma1*PI*D1^3)
650   L1=Lg1
660   !
670   Gamdlt=Gamma1+Delta
680   K5=15*Gamdlt*PI*Visc*Qbar/(8*K3*Qin*P)
690   Lg1=12
700   LOOP
```

```
710   Func1=(K5*(Lg1+Lp))-((Lg1+Lp)^(X-1)/(K4*(Lg1)^(1-Y)))^(1/(X-3))
720   EXIT IF ABS(Func1)<.00000001
730   Func2=(K5*(Lg1+Delta+Lp))-((Lg1+Delta+Lp)^(X-1)/(K4*(Lg1+Delta)^(1-Y)))^(1
/(X-3))
740   Lg2=Lg1-Delta*Func1/(Func2-Func1)
750   Lg1=Lg2
760   END LOOP
770   D2=K5*(Lg1+Lp)
780   N2=8*Qin/(15*Gamdlt*PI*D2^3)
790   L2=Lg1
800   !
810   Gam2dlt=Gamma1+(2*Delta)
820   K5=15*Gam2dlt*PI*Visc*Qbar/(8*K3*Qin*P)
830   Lg1=12
840   LOOP
850   Func1=(K5*(Lg1+Lp))-((Lg1+Lp)^(X-1)/(K4*(Lg1)^(1-Y)))^(1/(X-3))
860   EXIT IF ABS(Func1)<.00000001
870   Func2=(K5*(Lg1+Delta+Lp))-((Lg1+Delta+Lp)^(X-1)/(K4*(Lg1+Delta)^(1-Y)))^(1
/(X-3))
880   Lg2=Lg1-Delta*Func1/(Func2-Func1)
890   Lg1=Lg2
900   END LOOP
910   D3=K5*(Lg1+Lp)
920   N3=8*Qin/(15*Gam2dlt*PI*D3^3)
930   L3=Lg1
940   !
950   Fn1=8*Qin/(15*PI*Gamma1*D1^3)
960   Fn2=8*Qin/(15*PI*Gamdlt*D2^3)
970   Fn3=8*Qin/(15*PI*Gam2dlt*D3^3)
980   F11=8*K3*P*D1*Qin/(15*PI*Visc*Qbar*Gamma1)
990   F12=8*K3*P*D2*Qin/(15*PI*Visc*Qbar*Gamdlt)
1000  F13=8*K3*P*D3*Qin/(15*PI*Visc*Qbar*Gam2dlt)
1010  Beta1=(Fn2-Fn1)/Delta
1020  Beta2=(F12-F11)/Delta
1030  Beta3=(Fn3-Fn2)/Delta
1040  Beta4=(F13-F12)/Delta
1050  Func1=Beta1*(F11+2)+Beta2*(Fn1)
1060  EXIT IF ABS(Func1)<.00000001
1070  Func2=Beta3*(F12+2)+Beta4*(Fn2)
1080  Gamma2=Gamma1-Delta*Func1/(Func2-Func1)
1090  Gamma1=Gamma2
1100  END LOOP
1110  Gamma=Gamma1
1120  K5=15*Gamma*PI*Visc*Qbar/(8*K3*Qin*P)
1130  Lg1=12
1140  LOOP
1150  Func1=(K5*(Lg1+Lp))-((Lg1+Lp)^(X-1)/(K4*(Lg1)^(1-Y)))^(1/(X-3))
1160  EXIT IF ABS(Func1)<.00000001
1170  Func2=(K5*(Lg1+Delta+Lp))-((Lg1+Delta+Lp)^(X-1)/(K4*(Lg1+Delta)^(1-Y)))^(1
/(X-3))
1180  Lg2=Lg1-Delta*Func1/(Func2-Func1)
1190  Lg1=Lg2
1200  END LOOP
1210  De=K5*(Lg1+Lp)
1220  Nf=8*Qin/(15*Gamma*PI*De^3)
1230  Le=Lg1
1240  !
1250  Tmph=4.75+(.0976*Gamma)-(.00003*Gamma^2)+(3.51E-9*Gamma^3)
1260  Rh=Rp*(P+20)/Tmph
1270  Ae=Nf*PI*De*Le
1280  At=Nf*PI*De*(Le+Lp+2)
1290  Lspun=Nf*(Le+Lp+2)/10^5
1300  !
1310  PRINT USING 170;Nf,Le,10000*De,Ae,At,Rh,Lspun
1320  PRINT
1330  PRINT
1340  NEXT I
1350  !
1360  PRINT USING "@,5/"
1370  !
1380  END
1390  !
1400  DEF FNVisc(Hct)
1410  RETURN 3.236206/((1-(Hct/100))^1.440442)
1420  FNEND
1430  !
```

3 CYCLE DEVICES

Plasma volume collected........ 550 ml
Proceesing time................ 33.3 min

Blood volume drawn per cycle... 500 ml
Maximum Extracorporel Volume... 866 ml
Blood flow rate................ 90 ml/min Filtration Fraction............ 0.367
HCT............................ 45%
Efficiency..................... 0.667
Plasma Flow rate............... 33.0 ml/min
Potting length................. 2.5 cm

20

DEVICE INLET PRESSURE........... 50 mmHg

| N | L | D | Ae | At | Rh | Ls |
|---|---|---|---|---|---|---|
| 4332 | 7.00 | 208 | 1976 | 3247 | .54 | .498 |

DEVICE INLET PRESSURE........... 100 mmHg

| N | L | D | Ae | At | Rh | Ls |
|---|---|---|---|---|---|---|
| 2429 | 6.99 | 202 | 1076 | 1769 | .57 | .279 |

DEVICE INLET PRESSURE........... 150 mmHg

| N | L | D | Ae | At | Rh | Ls |
|---|---|---|---|---|---|---|
| 1731 | 6.99 | 198 | 754 | 1240 | .62 | .199 |

DEVICE INLET PRESSURE........... 200 mmHg

| N | L | D | Ae | At | Rh | Ls |
|---|---|---|---|---|---|---|
| 1361 | 6.99 | 196 | 586 | 963 | .69 | .156 |

DEVICE INLET PRESSURE........... 250 mmHg

| N | L | D | Ae | At | Rh | Ls |
|---|---|---|---|---|---|---|
| 1130 | 6.99 | 194 | 482 | 792 | .77 | .130 |

What is claimed is:

1. In a blood filtration system comprising
a hollow fiber membrane device for separating filtrate from blood comprising a housing having a blood inlet port, a blood outlet port, and a filtrate outlet port, the membrane device including a preselected number (N) of hollow fiber membrane elements carried within the housing, each element having a preselected length (L) and a preselected internal diameter (D), and apparatus associated with the hollow fiber membrane device for conveying blood having a determinable hematocrit ($H_i$) and viscosity ($\mu$) from a source through the blood inlet and outlet ports of the membrane device to therein separate filtrate from the blood and for conveying the filtrate from the filtrate outlet port of the membrane device, the apparatus including first means for establishing a flow rate ($Q_i$) of blood through the blood inlet port of the membrane device, second means for establishing a flow rate ($Q_f$) of filtrate from the filtrate outlet port of the membrane device, and third means for conveying filtrate-poor blood from the blood outlet port of the membrane device, a method of operating the system subject to a selected safety factor for red blood cell hemolysis (HSF) comprising the step of simultaneously obtaining the following performance relationships:

Performance Relationships (1) $Q_f = K_1 Q^x N^{(1-x)} L^{(1-y)} D^{(1-3x)}$ where
$K_1 = 0.0002206 [\ln(95/H_i)]^z H^{(1-x)} (8/15)^x$ and
$x = 0.9141$;
$y = 0.3619$;
$z = 0.8528$;
Q is the average blood flow rate through the device defined as the blood flow rate through the blood inlet port ($Q_i$) minus one-half the filtrate flow rate through the filtrate outlet port, or $Q_i - Q_f/2$; and
$H_i$ is the hematocrit (expressed in %) of the blood entering the blood inlet port of the device;

Performance Relationship (2)

$$Q = \frac{K_2 P N D^4}{\mu(L + L_p)}$$

where
$\mu$ is the blood viscosity function $= 3.236206/[(1-H_i)/100^{1.440442}]$;
$L_p$ is the potting length of the fibers, expressed in cm;
P is the pressure drop across the device expressed in mmHg; and $$K_2 = \frac{(\pi)}{(128)} \times$$

(the applicable conversion factor for consistent units);

and

Performance Relationship (3)

$$HSF = \frac{(TMP)_h}{P - (-20 \text{ mmHg})}$$

where $(TMP)_h =$ $$\frac{(3.51 \times 10^{-9} \gamma_{w,h}^3 - 0.00003 \gamma_{w,h}^2 + 0.0976 \gamma_{w,h} + 4.75)}{r_p};$$

$r_p$ is the average pore radius of the membrane; (−20 mmHg) is the assumed filtrate collection chamber pressure; and $$\gamma_{w,h} = \frac{8Q}{15 \, ND^3 \pi}$$

is the shear rate for hemolysis.

2. In a system according to claim 1, wherein the method of operation further includes the step of establishing a substantially constant pressure drop between the blood inlet and blood outlet ports.

* * * * *